United States Patent [19]

Langer et al.

[11] Patent Number: 4,891,225
[45] Date of Patent: Jan. 2, 1990

[54] BIOERODIBLE POLYANHYDRIDES FOR CONTROLLED DRUG DELIVERY

[75] Inventors: Robert S. Langer, Somerville, Mass.; Howard Rosen, Montara, Calif.

[73] Assignee: Massachusetts Institute of Technology, Cambridge, Mass.

[21] Appl. No.: 820,290

[22] Filed: Jan. 21, 1986

Related U.S. Application Data

[63] Continuation-in-part of Ser. No. 613,001, May 21, 1984, which is a continuation of Ser. No. 477,710, Mar. 22, 1983, abandoned.

[51] Int. Cl.$^4$ .................... A61M 31/00; A61F 5/46; A61K 31/78
[52] U.S. Cl. .................... 424/428; 424/427; 424/78; 424/409; 424/420; 528/271; 528/206; 528/207; 524/17; 524/21; 524/599
[58] Field of Search ............ 524/17, 21, 599; 424/19, 78, 427, 428, 409, 426; 528/271, 206, 207; 604/890, 891, 894

[56] References Cited

U.S. PATENT DOCUMENTS

| | | | |
|---|---|---|---|
| 2,071,250 | 1/1936 | Carothers | 160/106 |
| 2,071,251 | 1/1936 | Carothers | 18/54 |
| 2,073,799 | 3/1937 | Hill | 260/112 |
| 2,668,162 | 2/1954 | Lowe | 260/78.3 |
| 2,676,945 | 4/1954 | Higgins | 260/45.7 |
| 2,958,678 | 11/1960 | Conix | 260/78.4 |
| 2,960,493 | 11/1960 | Conix | 260/47 |
| 3,526,612 | 3/1966 | Allphin | 260/78.4 |
| 3,625,214 | 12/1971 | Higuchi | 128/260 |
| 3,766,145 | 10/1973 | Thompson | 260/75 EP |
| 3,811,444 | 5/1974 | Heller et al. | 128/260 |
| 3,914,401 | 10/1975 | Sharabash | 424/19 |
| 3,960,150 | 6/1976 | Hussain et al. | 128/260 |
| 3,976,071 | 8/1976 | Sadek | 128/260 |
| 3,981,303 | 9/1976 | Higuchi et al. | 128/260 |
| 3,986,510 | 10/1976 | Higuchi et al. | 128/260 |
| 3,993,071 | 11/1976 | Higuchi et al. | 128/260 |
| 4,014,987 | 3/1977 | Heller et al. | 424/15 |
| 4,036,227 | 7/1977 | Zaffaroni et al. | 128/260 |
| 4,070,347 | 1/1978 | Schmitt | 260/77.5 D |
| 4,096,238 | 6/1978 | Zaffaroni et al. | 424/15 |
| 4,489,056 | 12/1984 | Himmelstein et al. | 424/22 |

FOREIGN PATENT DOCUMENTS

| | | | |
|---|---|---|---|
| 684685 | 4/1964 | Canada . | |
| 2590262 | 5/1987 | France . | |
| 60-141725 | 7/1985 | Japan | 424/428 |
| 838986 | 6/1960 | United Kingdom . | |
| 840846 | 7/1960 | United Kingdom . | |
| 840847 | 7/1960 | United Kingdom . | |
| 968715 | 9/1964 | United Kingdom | 424/428 |

OTHER PUBLICATIONS

John E. Bucher and W. Clifton Slade, The Anhydrides of Isophthalic and Terephthalic Acids, *J. Amer. Chem. Soc.*, 32, 1319 (1909).

Naoya Yoda, Synthesis of Polyanhydrides, XI, *Makromol. Chem.* 36 (1962).

Naoya Yoda, Syntheses of Polyanhydrides, XII, Crystalline and High Melting Polyamidepolyanhydride of Methylenebis (p-carboxyphenyl)amide, *Journal of Polymer Science:* Part A, vol. I, 1323 (1962).

(List continued on next page.)

*Primary Examiner*—Robin Teskin
*Attorney, Agent, or Firm*—Kilpatrick & Cody

[57] ABSTRACT

A novel hydrophobic polymeric matrix is provided which is suitable for use after implantation in vivo in a subject for the controlled release and delivery of biologically active substances such as drugs, antibiotics, steroids and the like. Alternatively, the matrix can be used outside the body for release of fragrances, pesticides and the like. The implantable matrix comprises a polymeric polyanhydride formulation whose internal anhydride linkages are hydrolytic in nature in varying degrees in accordance with the chemical composition of the backbone, pH and temperature of the environment. As the individual anhydride linkages become hydrolyzed, the matrix erodes predominantly by surface erosion into non-toxic biocompatible degradation products with concomitant release of the biologically active substance.

17 Claims, 3 Drawing Sheets

OTHER PUBLICATIONS

Naoya Yoda, Synthesis of Polyanhydrides, II, New Aromatic Polyanhydrides with High Melting Points and Fiber-Forming Properties, *Makromol. Chem.* 32, 1 (1959).

Naoya Yoda, Synthesis of Polyanhyrides, X, Mixed Anhydrides of Aromatic and Five-Membered Heterocyclic Dibasic Acids, *Makromol. Chem.*, (1962).

Naoya Yoda and Akihisa Miyake, Synthesis of Polyanhdride, I., Mixed Anhydride of Aromatic and Aliphatic Dibasic Acids, *Makromol. Chem.* 32 (10), 1120 (1959).

Julian W. Hill and Wallace H. Carothers, Studies of Polymerization and Ring Formation, XIX, Many--Membered Cyclic Anhydrides, *J. Amer. Chem. Soc.* 55, 5023 (1933).

A. Conix, Poly[1,3-bis(p-carboxyphenoxy)-propane anhydride], *Macromolecular Syntheses*, vol. two, 95 (1966).

Julian W. Hill and Wallace H. Carothers, Studies of Polymerization and Ring Formation, XIV, A Linear Superpolyanhydride an a Cyclic Dimeric Anhydride from Sebacic Acid, *J. Amer. Chem. Soc.*, 54, 1569 (1932).

Polyanhydrides, *Ency. of Poly. Sci. & Tech.* 10, 630 (1969).

K. W. Leong, B. C. Brott and R. Langer, "Bioerodible Polyanhydrides as Drug-Carrier Matrices, I: Characterization, Degradation, and Release Characteristics", *Journal of Biomedical Materials,* Research 19, 941 (1985).

K. W. Leong, P. D'Amore, M. Marletta and R. Langer, "Bioerodible Polyanhydrides as Drug-Carrier Matrices, II, Biocompatibility and Chemical Reactivity", *Journal of Biomedical Materials Research* 20, 51 (1986).

"Synthesis of Polyanhydrides X, Mixed Anhydrides of Aromatic and Five-Membered Heterocyclic Dibasic Acids", by Naoya Yoda in *High Polymer Chem.*, Japan 10-35 (1962).

"Bioerodible Polyanhydrides as Drug-Carrier Matrices, I: Characterization, Degradation, and Release Characteristics", by K. W. Leong, Brott, & Langer in *J. Biomed. Mtls. Res.*, 19,941-955 (1985).

Rosen, MIT thesis dated Jan. 14, 1982, "Synthesis and Characterization of Bioerodible Polymer for Controlled Drug Release".

Rosen et al., *Biomaterials*, vol. 4, Apr. 1983, pp. 131-133, "Bioerodible Polyanhydrides for Controlled Drug Delivery".

Cottler et al., *Chemis Weckblud*, vol. 63 (1967), p. 113.

fig. 1 fig. 2 fig. 3 fig. 4 fig. 5

BIOERODIBLE POLYANHYDRIDES FOR CONTROLLED DRUG DELIVERY

SUPPORT AND APPLICATION HISTORY

The invention described herein was made with the support from a grant or an award from the National Institute of Health, GN26698. This application is a continuation-in-part of application Ser. No. 613,001, filed May 21, 1984, which was a continuation of application Serial Number 477,710 filed March 22, 1983, now abandoned.

BACKGROUND OF THE INVENTION

In recent years, much research has been directed to developing polymeric compositions and delivery systems for the programmed release of biologically active agents, especially drugs, over preselected periods of time. The purpose of these programmed release systems is to dispense the biologically active substance at a controlled and, preferably, constant rate after implantation into a subject in vivo. A common illustration is the release of pharmaceutically active drugs using such programmed release systems to improve a therapeutic regimen by delivering the drug in a beneficial and reliable manner and with minimum potential for complications or failure to provide adequate dosage.

Although controlled release of biologically active substances has been accomplished in several ways, a mechanism utilizing biodegradation of an implanted polymeric matrix into soluble degradation products provides the distinct advantage of eliminating the need for subsequent surgical removal of the article after implantation. However, despite desirability of such a mechanism, the development of polymeric matrix systems using bioerodible polymers for controlled release of active agents has not progressed quickly. In fact, few bioerodible polymers have been developed for biomedical or in vivo use; of these, a very few polymeric formulations were designed specifically for the release of biologically active substances in a controlled manner. One example is described in U.S. Pat. No. 4,070,347 which provides polycarbonate and polyorthoester polymeric compositions but which fails to identify formulations with active agents or evidence of performance of actual drug delivery. The general absence of polymeric compositions suitable for implantation in vivo and which are bioerodible into soluble, nontoxic products has increased the difficulties and problems encountered in developing effective matrices for the controlled release of active substances. This is best illustrated by the fact that no bioerodible polymeric system has yet received final approval by the Food and Drug Administration for release of a biologically active agent in clinical or therapeutic applications.

The ideal situation for controlled release of a biologically active substance by a bioerodible polymeric matrix system is one where the active substance is uniformly distributed throughout a polymeric matrix and where biodegradation by surface erosion is the determining factor for release of the substance to occur. As part of this ideal situation, the polymeric matrix would erode at a preselected, constant rate and the biologically active substance would then be released at a zeroorder rate, a rate in which the active substance is released without regard to the concentration of any other chemical component. Kinetically, if a constant erosion rate (k) is obtained, the release rate for the biologically active substance (dM/dt) from the polymeric matrix will be equal to the arithmetic product of (k) and the surface area (provided by the configuration and geometric dimensions) of the polymeric matrix, provided there is no diffusional release. Accordingly, in order to obtain a zero-order release reaction of active substance from the matrix, it becomes necessary to utilize a matrix geometry which does not substantially change in surface area as a function of time. Such an ideal system would also possess the following advantages: a simple release mechanism which is independent of the pharmaceutical properties provided by the active substance; an ability to vary the release rate of active substance linearly by linearly altering the concentration of active substance within the matrix; a conservation of polymer matrix mechanical integrity because erosion occurs only at the surface of the matrix; an ability to linearly vary the effective use life of the matrix release system by either increasing or decreasing the thickness of the matrix; and in vivo formation and elimination of the polymeric degradation products concomitant of the released biologically active substance.

The ideal delivery system as described herein has never been found to exist in practice. Almost invariably, the polymeric matrix composition does not degrade into low molecular weight, non-toxic products, does not provide zero-order release reactions for the active substance and does not present constant erosion rates. Worse still, bulk erosion of the polymeric matrix often occurs in addition to or in place of surface erosion which renders the entire polymer composition spongelike and causes breakup of the matrix; in addition, bulk erosion causes great difficulties in both controlling the rate of active substance release because of multiple release kinetics phenomena (such as diffusion and concentration gradients) and in achieving a zero-order release reaction.

The cause of bulk erosion is directly due to the hydrophilic nature of almost every bioerodible polymeric composition which has been developed for biomedical use. Hydrophilic bioerodible polymers characteristically imbibe water which is drawn into the center of the matrix. This characteristic is both expected and desired since most bioerodible polymers developed for biomedical use were intended for use as suture materials and the like rather than as matrices containing concentrated quantities of biologically active substances for subsequent controlled release of the active substances. Polymers recognized as eroding by bulk erosion include polylactic acid, polyglutamic acid, polycaprolactone and lactic/glycolic acid copolymers [Pitt et al, Biomaterials 2:215–220 (1981); Koenig et al, J. Macromol. Sci. Phys. 2:391–407 (1966].

One solution to the problem of bulk erosion is the preparation and use of hydrophobic polymeric compositions. The only bioerodible hydrophobic polymer which has been formulated for use in systems for delivery of biologically active substances are polyorthoesters. An example of such polyorthoesters having a carbonyloxy functionality is described in the previously identified U.S. Pat. No. 4,070,347. As has been recognized, their advantages lie in that not only are they hydrophobic, but also that hydrolysis of orthoester is pH sensitive, a property which has been proven useful in regulating the release of active substance.

However, although different kinds of polyorthoesters have been synthesized, they uniformly possess certain disadvantages [Heller et al, *Polymer Eng. Sci.* 21:727-731 (1981)]: by themselves, polyorthoesters are often too hydrolytically stable for use in controlled release systems; often only 7% by weight of the polymer erodes in more than 220 days. Such matrices, therefore, require inclusion of acid catalysts within the matrix to promote bioerosion. Second, polyorthoester polymers swell substantially when attempts are made to suppress degradation in the interior of the matrix by incorporating sodium carbonate into the polymeric matrix, the rate of swelling often dominating and affecting the rates of release for the active substances more than the rate of erosion itself. Finally, the degradation products of polyorthoester polymeric release systems are not as simple as those using hydrophilic polymeric systems (such as polylactic acid matrices) which have the added advantages that the ultimate degradation products are water and carbon dioxide.

Overall, therefore, there remains a demonstrated need for a hydrophobic bioerodible polymeric matrix system for the controlled release of biologically active substance where the release occurs by surface erosion and the eroded intermediate and final degradation products are non-toxic and readily eliminated by the body in vivo. Such a programmed release system should not cause adverse tissue reactions within the body in vivo, should exhibit mechanical and physical integrity of the polymeric matrix, should not require additives and provide release of the active substance by a controllable kinetic mechanism. In addition, it is preferred that the matrix comprising such a delivery system be easily polymerized, be formable into predetermined geometric dimensions and remain stable upon storage under a variety of conditions.

SUMMARY OF THE INVENTION

A hydrophobic polymeric matrix useful for the controlled release of biologically active substances after implantation in vivo or utilized outside the body is provided comprising a polyanhydride polymer having the formula $(COROCO)_n(COR'OCO)_m$ where r and R' are selected from the group consisting of hydrocarbons and organic compositions having a molecular weight not substantially greater than 500 daltons, m and n are at least 1; and at least one biologically active substance. The matrix is suitable for implantation in vivo and is preferably made by preparing a hydrophobic polyanhydride polymer $(COROCO)_n(COR'OCO)_m$ pulverizing the polyanhydride polymer into a particle mass, combining the particle mass with the biologically active substance as a mixture and compressing this mixture under heat and pressure to form a solid matrix having a predetermined configuration and geometiric dimensions. After surgical implantation into a subject in vivo, the hydrophobic matrix erodes by surface erosion to release and deliver the biologically active substance into the body at a substantially constant rate and as a substantially zero-order release reaction.

DETAILED DESCRIPTION OF THE DRAWING

The present invention may be more completely and easily understood when taken in conjunction with accompanying drawing, in which.

DETAILED DESCRIPTION OF THE PREFERRED EMBODIMENTS

The present invention comprises three major aspects: an article of manufacture, a hydrophobic polymeric matrix containing at least one biologically active substance, which is useful as a controlled delivery system for release of the active substance, a method for preparing the hydrophobic polymeric matrix containing the biologically active substance and a method for the controlled release of biologically active substances in vivo using the hydrophobic polymeric matrix as an article suitable for implantation in vivo. It will be recognized that each part of the invention is dependent upon the existence and use of the other parts and that each definition of the invention is merely an alternate form of the single invention as a whole.

The hydrophobic polymeric matrix is an article of manufacture comprising a hydrophobic polyanhydride polymer having the formula where R and R' are selected from the group consisting of hydrocarbons and organic compounds of low molecular weight, preferably not substantially greater than 500 daltons, and m and n are not less than 1 and preferably are at least 10. The polyanhydride polymer which may be itself subsequently polymerized with other reactants may alternatively comprise a homopolymer (where R=R') or a copolymer (where R≠R'). Prepolymer anhydrides comprising the copolymer may be combined in any ratio; in addition, each anhydride component comprising a copolymer may be individually polymerized to any degree. More than one homopolymer or copolymer may be used to form the polymer and each may be used in a regular pattern, in cyclican sequences or at random.

The individual anhydride prepolymers themselves, regardless of their specific formulation or degree of internal polymerization, may be either hydrophilic or hydrophobic in accordance with the users' expected needs or desires. Nevertheless, because it is required that the final polyanhydride polymer be substantially hydrophobic in character, it is preferred that the prepolymers be themselves hydrophobic in some measurable degree. It will be recognized also that the hydrophobicity of the prepolymers can be adjusted and regulated by selective choice of the R and R' moieties, by altering the ratio and degree of polyanhydride polymerization within the prepolymer itself and by varying the degree of prepolymer polymerization.

The selection of R and R' will directly influence the hydrophobicity of each homopolymer and copolymer and, concomitantly, of the polymeric matrix composition. The identity of R and R' may include: alkyl and aryl hydrocarbons containing from 1-20 carbon atoms, heteratom organic compounds having from 1-20 carbon atoms, aromatic organic moieties such as p-carboxyphenoxy methane, its homologues and derivatives, substituted and unsubstituted benzenes, heterocyclic aromatic compositions such as pyridine and its derivatives. It will be appreciated, therefore, that R and R' are linking moieties of low molecular weight, preferably less than 500 daltons. It is preferred that the R and R' ntities be themselves hydrophobic in nature, but this is not an absolute requirement so long as the polymerized matrix composition demonstrates a substantial degree of hydrophobicity. Since the anhydride linkage between monomer units in the copolymer is highly reactive towards hydrolysis, it is, therefore, preferable that the monomers comprising the polymer backbone also be formed as hydrophobic compositions in order to create the requisite conditions for surface erosion of the polymeric matrix and a zero-order release reaction mechanism.

The biologically active substances which can be utilized with the polyanhydride polymer to form the matrix may be selected from the entire known range of biologically and/or pharmacologically active substances including drugs, vitamins, enzymes, antigens, antibodies, proteins and the like without limitation. The precise biological activity or nature of its function in vivo is immaterial so long as the substance is capable of being intimately mixed with the polyanhydride polymeric matrix without adverse physical or chemical reaction and of being subsequently formed into a specific configuration and preset geometric dimensions without substantially affecting the activity of the substance. Accordingly, the biologically active substance may be a protein, a polypeptide or it may be non-proteinacious. It may be a macromolecule (greater than 500 daltons in molecular weight) or be a low molecular weight compound (having a molecular weight not greater than 500 daltons). The substance may be soluble, slightly soluble or insoluble in water. A non-comprehensive listing of representative examples, therefore, includes without limitation: interferon, anti-angiogenesis factors, antibodies, antigens, polysaccharides, growth factors; hormones including insulin, glycogen, parathyroid and pituitary hormones; calcitonin, vasopressin, renin, prolactin, growth hormones, thyroid stimulating hormones, corticotrophin, follicle stimulating hormones, luteinizing hormones, corionic gonadotropins; enzymes including soy beam trypsin inhibitor, lysozyme, catalase, tumor angiogenesis factor, cartilage factor, transferaces, hydrolases, lysases, isomerases, proteases, ligases; oxidoreductases such as esterases, phosphatases, glycosidases and peptidases; enzyme inhibitors such as leupeptin, antipain, chymostatin and pepstatin; and drugs such as steroids, anticancer drugs, antibiotics, prostaglatins and the like.

The relative proportion and/or concentration of biologically active substance which is combined with the polyanhydride polymer to form the hydrophobic matrix will reflect four factors: the total time during which the matrix is desired to be effective, the desired rate of release for the active substance from the matrix, the intended site where the matrix is to be implanted in vivo and the minimum dosage of active substance which, after release, will be therapeutically effective. The use of the hydrophobic matrix as a system for delivery of biologically active substances at a preselected site and in a controlled manner inherently relies upon the release of multiple dosages of concentrated active substance over an extended time period. For this reason, the proportion of biologically active substance may range from about 1-50 parts by weight per 100 parts by weight of matrix material to be implanted. The amount of polyanhydride polymer may thus vary from 99-50 parts also. In most instances, however, from about 10-30 parts by weight of biologically active substance per 100 parts of matrix materials by weight is sufficient. These stated proportions of biologically active material to polyanhydride polymer mass are useful without regard to the degree of polymerization within either the copolymer or final composition, the molecular weight of the component units or the molecular weight of the final polymerized material, and without regard to the specific moieties selected for use as R and R'. By basing the proportional quantity by weight of biologically active substance with respect to 100 parts by weight of matrix material, it is intended and expected that persons ordinarily skilled in the art may prepare a wide variety of polyanhydride polymeric compositions and combine each with a biologically active substance of choice without hardship, inconvenience or undue experimentation.

The entire class of polyanhydride polymers can be synthesized using alternative methods of polymerization now known in the art: bulk polymerization [Conix, A., Macro Synth. 2:9598 (1966)], solution polymerization [Yoda et al, Bull. Chem. Soc. Japan 32:1120-1129 (1959)]and interfacial polymerization [Matsuda et al, Japanese Patent No. 10,944 (1962)]. Using any of these methods, a variety of different synthetic polymers having a broad range of mechanical, chemical and erosion properties are obtained; the differences in properties and characteristics are controlled by varying the parameters of reaction temperatures, reactant concentration, types of solvent and reaction time. This is true for all potential embodiments of R and R' within the general formula stated above as well as the specific embodiments described in the Examples which follow herein.

The preferred method of preparing the hydrophobic polyanhydride polymer is a modification of the melt polycondensation synthesis method of Conix [*Macro Synth.* 2:95-98 (1966)]in which the prepolymer is recrystallized initially to provide a more pure, higher molecular weight unit for polymerization. In general, dicarboxylic acid compositions comprising R and/or R' of choice are obtained from commercial sources or synthesized in the laboratory by well-known methods. These dicarboxylic acids comprising R and/or R' are combined with excess acetic anhydride and converted to the anhydride forms respectively by total reflux. Care should be taken to avoid an excessive reflux reaction which will yield a highly insoluble prepolymer which is difficult to purify; for this reason, reflux time of 30 minutes to 2 hours is considered adequate. The reflux reaction product yields prepolymers which can be directly isolated from the reaction mixture in the conventional manner and recrystallized using a 50:50 (volume/volume) mixed solvent of acetic anhydride and dimethylformamide. A recrystallization period of several weeks duration was sometimes necessary to obtain a yield of approximately 30%. The prepolymers then underwent melt polycondensation in vacuo under a nitrogen sweep environment as in the conventional methods, to yield the hydrophobic polyanhydride polymers.

It will be noted that the preferred melt polycondensation synthesis technique as modified allows the user to prepare polyanhydride polymers of widely different formulations and molecular weights and allows the user to control the degree of polymerization to meet individual requirements or preferences. If the user desires precise knowledge of the molecular weight of the prepolymers or copolymers, the degree of polymerization, and the molecular weight of the final polyanhydride polymeric composition itself, techniques for making these determinations are within the common knowledge of practitioners ordinarily skilled within this art and, for this reason, need not be described in detail herein. It will be explicitly recognized, however, that the degree of polymerization, the molecular weight and the methods by which these determinations are made are immaterial to the present invention; all of these are individual matters of knowledge, choice or convenience which in no way influence or limit either the utility of the present invention or the wide variety of embodiments which are within the scope of the invention as defined.

To form the polymeric matrix, a biologically active substance of choice, such as a drug, is added to the polyanhydride polymer in the above-identified ratios to form a mixture, and this mixture subsequently shaped into a specific configuration having set geometric dimensions. The manner in which the biologically active substance is combined with the polyanhydride polymer utilizes conventionally known techniques. For example, one suitable method for making the matrix material comprises dissolving the polyanhydride in an appropriate solvent such as anhydrous ether to form a casting solution. A desired amount of biologically active substance comprising up to 50% by weight is then added to the casting solution and blended with the polyanhydride polymer until a homogenous liquid is obtained. This homogenous liquid is then poured into a prepared mold having a specific configuration and having set geometric dimensions. The liquid within the mold is then allowed to dry and harden, usually under vacuum, thereby causing the polyanhydride polymer to precipitate and solidify with concomitant retention of the biologically active substance as an internal phase. In this manner, the hydrophobic polymeric matrix is formed in the predetermined form and size which is useful for the controlled release of the biologically active substance after the matrix has been implanted in vivo.

The preferred method of forming the hydrophobic matrix first purifies the polyanhydride polymers by extraction with anhydrous ether in a Soxhlet Extractor for several hours and then stores the purified polymers in a desiccator over calcium chloride. The purified polymers are thus a crystalline solid material which is then ground in a Micro Mill Grinder and sieved into a particle size ranging from 90–150 micrometers (hereinafter um). The polyanhydride powder is then admixed with the desired quantity of biologically active substance which also is in the form of a sieved powder or other particular solid. This admixture of anhydride polymer particles and biologically active substance particles is then pressed into a specific configuration and set dimensions using molding equipment such as a Carver Test Cylinder Outfit at 30 KPSI at 5° C. above the polymer's glass transition temperature for approximately 10 minutes. For those polymeric compositions which had a glass transition temperature below 30° C., these were molded in suitable equipment at room temperature. If desired, the temperatures and pressures may be adjusted to accommodate the equipment available to the user and to achieve the desired shape and dimensions.

In addition to these methods, other methods of combining the polyanhydride polymer with the biologically active substance of choice may be used which employ injection methods, compression methods, extrusion methods or any combination of these. It will be appreciated that although the preferred method is the admixture of pulverized polyanhydride polymer and pulverized biologically active substance with subsequent molding to a specified shape using heat and pressure, any other method, technique or equipment which provides hydrophobic polymeric matrix in which the biologically active substance is interspersed without substantial deterioration or alteration of its biological activity is suitable with the invention.

The configuration and dimensions using the preferred admixture of polymer and biologically active substance powders is the formation of a mass which is substantially a slab in configuration. The slab can be in fact circular, oval, rectangular or the like in shape. Preferred dimensions of the disc are between about 1 mm and 10 mm in thickness, and have a diameter between about 0.01–2.00 centimeters, and preferably have a total surface area between about 1 square centimenter and about 100 square centimeters. Matrices shaped in this configuration have demonstrated a zero-order release reaction mechanism and a regular release of the biologically active substance over time. It will be appreciated that the configuration and dimensions of the matrix itself are matters of individual choice or need; accordingly, the matrix may be configured in a wide range of shapes, size and forms to meet the specific applications, sites of intended implantation, or environment of use.

To demonstrate the range of hydrophobic polymeric matrices which may be prepared using a wide range of polyanhydride polymers and biologically active substances, the following examples are provided. It will be explicitly understood and appreciated, however, that these examples are merely individual illustrations and embodiments of the invention as a whole and in no manner restrict or limit the present invention in any way. It is also intended and expected that practitioners ordinarily skilled in the art, after following the teachings of these specific examples and the description of the subject matter as a whole which comprises the present invention, will recognize and appreciate that the hydrophobic polymeric matrix comprises polyanhydride polymers generally without regard as to the specific compositions forming the prepolymer units. It is thus immaterial whether the prepolymers themselves comprise various amino acids, alkyl groups, aromatic groups or any other class or specific formulation. Similarly, the range of biologically active substances is understood and intended to be viewed generally without regard to the nature, function or therapeutic utility of a particular compound. Accordingly, the hydrophobic matrix material includes all biologically active substances as a whole and is not to be viewed or evaluated toward specific antibiotics, steroids, drugs and the like as recognized functional equivalence. Given this understanding of the invention as a whole the following examples identify the preferred embodiments and applications of the invention.

EXAMPLE I

Poly[bis(p-carboxyphenoxy)methane]hereinafter "PCPM" was chosen as the prototype to demonstrate the usefulness of polyanhydride polymers as matrices for the controlled release of biologically active substances. The PCPM homopolymers were prepared by the modification of the Conix methodology previously described [*Macromolecular Synthesis* 2:95-98 (1966)]. The modification is a recrystallization of the prepolymer to yield a more pure product, prior to formation of the homopolymer. Accordingly, 0.3 moles of bis(p-carboxyphenoxy)methane, the dicarboxylic acid precursors of (p-carboxyphenoxy)methane were combined with 600 ml of acetic anhydride and converted to the prepolymer anhydride form by total reflux for 30 minutes. Caution was taken to avoid excessive reflux reaction which would yield a highly insoluble prepolymer more difficult to purify. The prepolymers isolated were further purified by recrystallization in a 50:50 (v/v) mixed solvent of acetic anhydride and dimethylformamide. The recrystallization period was sometimes extended to several weeks in order to obtain a reasonable yield of 30% or more. The prepolymers then underwent melt polycondensation in vacuo under nitrogen sweep. The resulting PCPM polyanhydride was a yellow, translucent, amorphous solid having a glass transition temperature of 92° C. Testing by infrared spectroscopy demonstrated that this PCPM polymer had carbonyl stretching frequencies of 1770 and 1720 centimeters respectively. No attempt to evaluate the degree of polymerization or the molecular weight of the final PCPM polymer was made; such information was deemed to be unimportant with respect to the characteristics of PCPM which made it useful as a matrix for delivery of biologically active substances.

Matrices comprising PCPM were formulated either by compression or injection molding, each being deemed equivalent to the other. For evaluation purposes, two kinds of matrices were prepared: a PCPM matrix without any biologically active substance whatsoever, and a PCPM matrix containing cholic acid. To formulate the PCPM matrices without any active substance, purified PCPM polymer in the solid crystalline form was ground into a pulverized powder using a Micro Mill Grinder (Fisher Scientific) and sieved into sized particles ranging from 150300 micrometers (hereinafter "um") in diameter. The polymeric particles were then compressed into circular disc configurations using a Carver Laboratory press in the following manner: the PCPM particles were placed between sheets of aluminum foil and subjected to temperatures ranging from 93° C.-116° C. and pressures ranging from 22kpa-81kpa, using shims to regulate the thickness of the disc being formed. It was found that applying temperatures below 120° C., the pulverized PCPM did not flow well and thus yielded matrices with poor mechanical properties; on the other hand, using temperatures above 145° C., many of the matrices formed were found to be brittle. In addition, there were no discernable differences in the properties of the matrices when pressed within the range 22 - 81 KPSI. Accordingly, the conditions chosen for forming the matrix were 121° C. and 22 KPSI consistently when molding PCPM polymer. These molding conditions gave matrices with useful mechanical properties and minimized the possibilities of morphological changes within the polymer during the molding process. A series of PCPM matrices were then prepared in disc shape configurations whose face surface are ranged from 0.2-0.8 square centimeters and had a thickness ranging from 0.05-0.10 centimeters.

To prepare PCPM matrices containing cholic acid, a blend of unlabelled and tritiated cholic acids were used. Specifically, unlabelled cholic acid in 15 milligram concentrations was dissolved in 10.0 milliliters (hereinafter "ml") of ethanol. Tritiated cholic acid (2.4–3.0 H) in sufficient quantities was dissolved in 125 microliter (hereinafter "ul") of ethanol to provide a $3.75 \times 10^{10}$ DPM/mg concentration. The tritiated solution and the mixture dried in vacuo. The mixture of cholic acids in powder form was added at 10.5 weight percent to the pulverized PCPM prepared as previously described and meltpressed at 121° C. and 22 KPSI as earlier described to yield a disc shaped matrix. This matrix was then sandwiched between two very tin (less than one weight percent) layers of PCPM (150-33 um diameters) and heat compressed to form a single article. The use of PCPM as sandwich layers eliminated the presence of cholic acid particles at the surface of the matrix and provided a PCPM initial exterior surface identical to those matrices containing no cholic acid whatsoever.

Each of the PCPM matrices with and without cholic acid were evaluated by in vitro erosion studies. In each instance, the matrices in disc form weighing from 10-50 mg were placed in glass scintillation vials containing 10 ml of 0.2 M phosphate buffer (pH 7.4) at a temperature of 37° C. or 60° C. The buffer was periodically changed by removing the matrix from the vial and placing it in another vial containing fresh buffer. Each of the buffer solutions were then collected and the absorbence at 2434 nanometers (hereinafter "NM") using a Gilford spectrophotometer to detect the presence of the diacid monomer, bis(p-carboxyphenoxy)methane in the liquid. Those buffer solutions containing tritiated cholic acid-containing matrices were analyzed for the presence of tritiated cholic acid using a LS-230 Beckman scintillation counter. The results are graphically illustrated by FIGS. 1-5.

Figure 1:
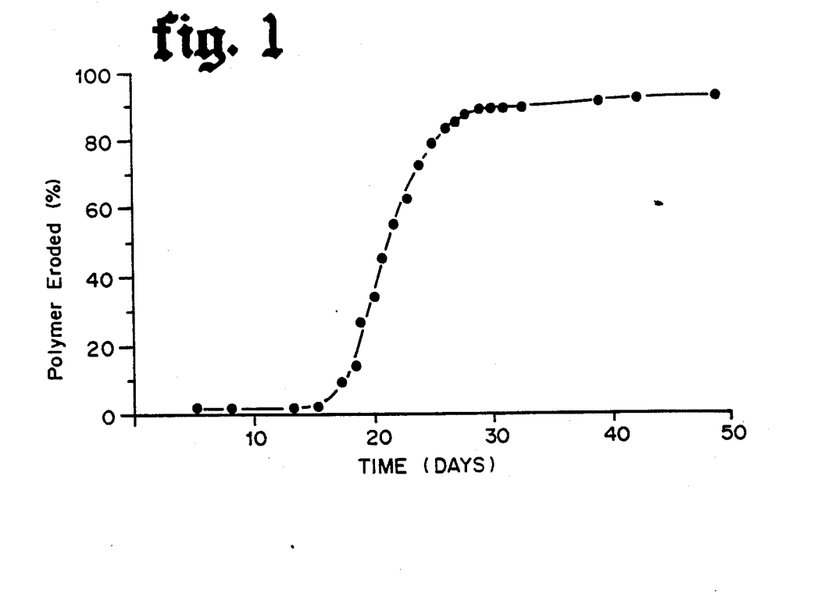
FIG. 1 is a graph illustrating the erosion rates of poly (p-carboxyphenoxy) methane polymer matrices at 37° C. over time.
Figure 2:
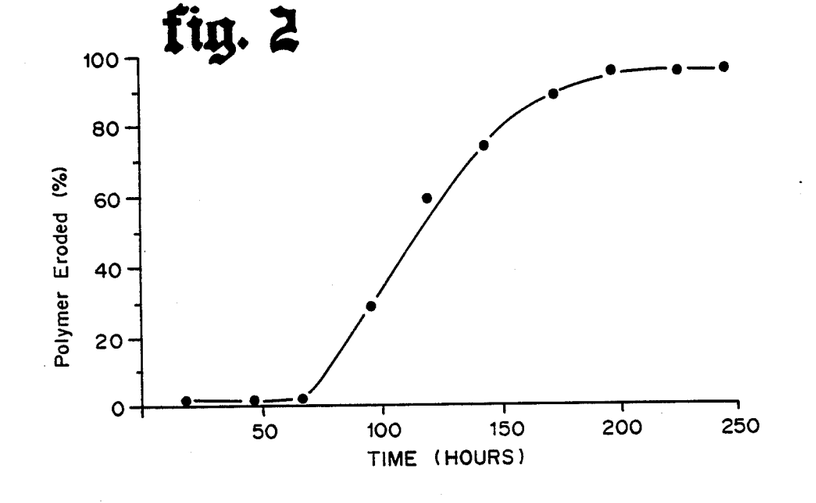
FIG. 2 is a graph illustrating the erosion rates pf poly (p-carboxyphenoxy) methane polymer matrices at 60° C. over time.
Figure 3:
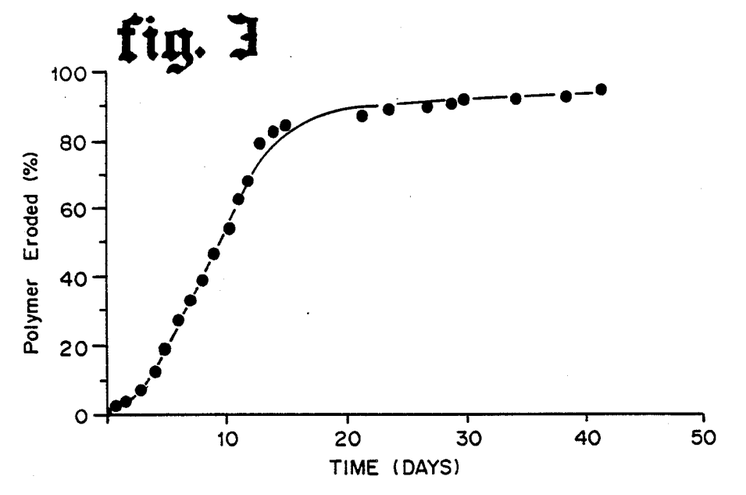
FIG. 3 is a graph illustrating the erosion rates of poly (p-carboxyphenoxy) methane polymer matrices which have been pre-eroded at 60° C. for 50 hours and then placed in 37° C. environments.
Figure 4:
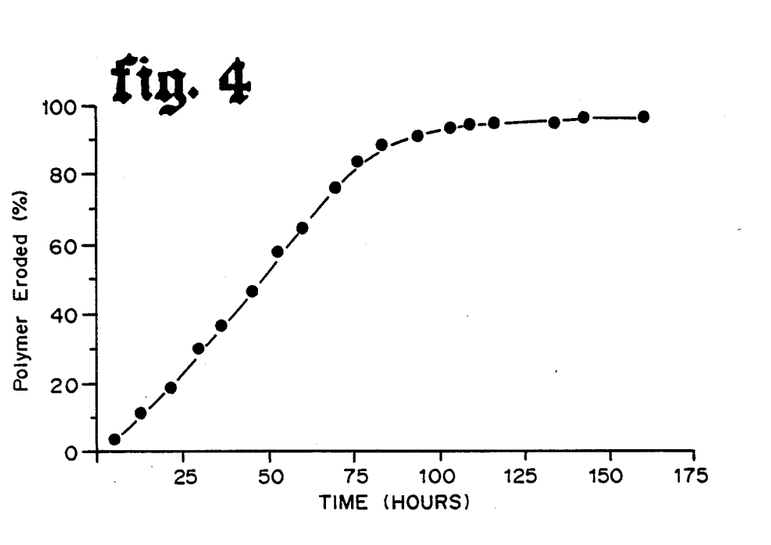
FIG. 4 is a graph illustrating the erosion rates of poly (p-carboxyphenoxy) methane polymer matrices which have been pre-eroded at 60° C. for 50 hours and continued at 60° C.

FIGS. 1 and 3 demonstrate the erosion curves for PCPM matrices without any cholic acid in phosphate buffer at 37° C. and 60° C. respectively. The weight of the matrices tested at each temperature weighed 23 and 18 milligrams; it is noted that the rate of surface erosion as much slower at 37° C. than when placed at 60° C. FIGS. 3 and 4 illustrate the effect of preeroding PCPM matrices at 60° C. for 50 hours prior to being placed in 37° C. and 60° C. environments for a more extended time. The matrices tested at 37° C. and 60° c. weighed 74 and 25 milligrams respectively. It will be noted that the polymer erosion in each and every instance was 100% of the total mass of the matrix regardless of the time required for such surface erosion to be complete. In all instances as well, each matrix decreased in size and maintained their physical integrity throughout the entire duration of the test demonstrating that only surface erosion of the matrix occurred. It is also appreciated that in all instances the erosion rate is characterized by an induction period which is then followed by a linear loss of mass at a constant rate. All the empirical evidence thus demonstrates that a zero-order erosion reaction is in effect.

Figure 5:
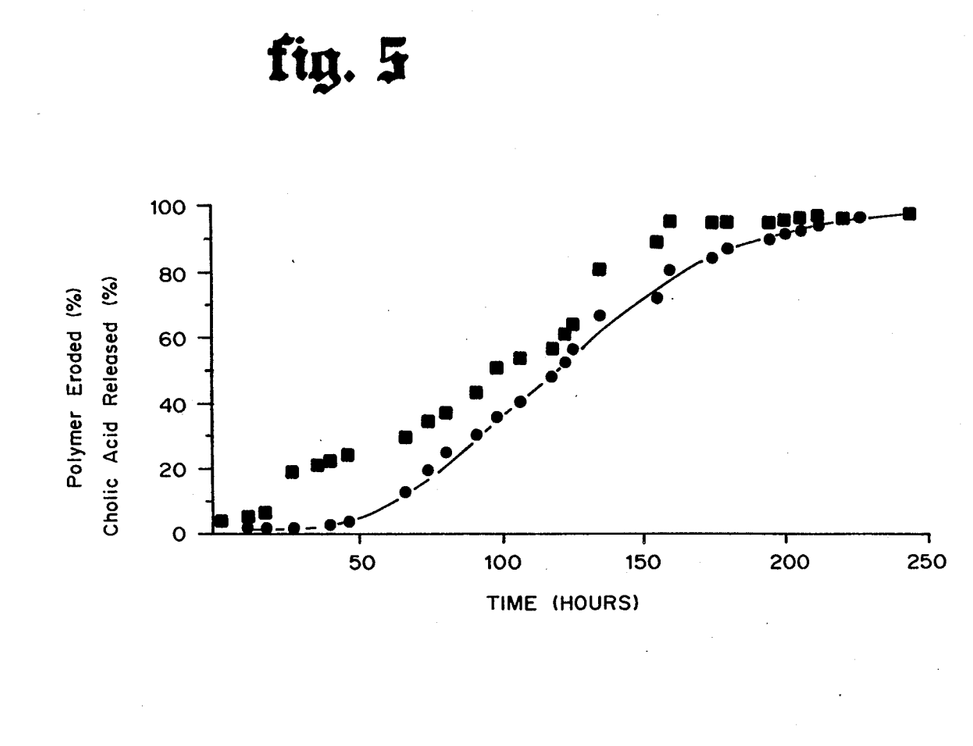
FIG. 5 is a graph illustrating the erosion and release rate for poly (p-carboxyphenoxy) methane polymer matrices containing 10.5 weight percent cholic acid.

Similar tests for PCPM matrices containing cholic acid at 10.5 weight percent were conducted in phosphate buffer held at 60° C. The results are illustrated by FIG. 5. The rate of erosion for the PCPM matrix indicated by the circular solid dots follows the rate of cholic acid release indicated by the solid square boxes. Each matrix weighed 25 milligrams initially and eroded completely (100%) within 250 hours duration at 60° C. It is noted that there is also a short induction period followed by a linear loss of mass and release of cholic acid at a constant rate. A comparison of the profiles between FIGS. 1-4 and FIG. 5 reveals a nealy zero-order reaction in all instances and linear loss of mass at constant rates which are very similar.

An in vivo erosion study was also performed using three matrices cut from a single melt-pressed PCPM slab, each matrix having a 0.26 square centimeter face surface area, 0.069 centimeters in thickness, and weighing 24 milligrams. Each matrix was essentially square in configuration and each was sterilized using UV light for 30 minutes prior to implantation into the test animal. Sprague-Dawley rate of comparable age and weight were used as the test animals. Each square was implanted subcutaneoulsy in the abdominal region of each rat by surgical procedure and cared for normally thereafter with adequate food and water. Animals were sacrificed at the end of 21, 44 and 153 days after implantation. The matrix was then removed from the site of implantation, dried and weighed. The results showed that in vivo erosion of PCPM rectangular slabs without any biologically active substance demonstrated a half life of about 47 days, a period approximately 5 days less than the life expectancy demonstrated by in vitro erosion at 347° C. Also, after 153 days, it was found that less than 1% of the matrix remained intact. Finally, the matrices at the site of implantation were found to be only slightly encapsulated by the tissues of the animal.

EXAMPLE II

The properties of the poly[bis(p-carboxyphenoxy)-propane]as a matrix for the controlled release of a biologically active substance were also evaluated. PCPP was synthesized as described in Example I and in the general discussion by conversion of its dicarboxylic acid precursor to a mixed anhydride followed by thermal condensation of the mixed anhydride into the polymeric form following the procedure of Cottler et al [*Chemis Weekblad* 63:113 (1967)]. The PCPP prepolymers were purified by recrystallization in acetic anhydride repeatedly until a snowy white prepolymer was obtained. Were this repeated recrystallization step not done, the polymer would appear as a dark brown solid as a result of contamination and decomposition during the polymerization process conducted at high temperature. After purification in this manner, the white prepolymer in a polymerization tube was immersed in a paraffin oil bath in a dry nitrogen environment under dynamic vacuum of less than 1 torr. The polymer thus-obtained was only slightly yellow and crystalline in structure.

Using methods of gel permeation, chromatography and solution viscometry, the polymer was demonstrated to have an average weight molecular weight of 15,000 daltons and a polydispersity of 3.6. Molecular weight species less than 15,000 daltons dissolved in tetrahydrofuran, dimethylformamide and other polar solvents. The glass transition temperature and melting temperature obtained using DSC measurements were 92° C. and 240° C. respectively.

The PCPP polymer was the pulverized into particles 150-330 um in diameter and compression molded into this slabs whose dimensions varied from face surface areas of 0.2-3.0 3.0 aquare centimeters, a thickness of 0.05-0.10 centimeters, and had an average weight of 24 milligrams. The compression was conducted at 150° C. and at 50 KPSI. These slabs were then placed in vials containing phosphate buffer at 37° C. but whose pH ranged from 1.0-11.0. The in vitro erosion rates were then determined as in Example I. The results indicated that the rate of erosion for the PCPP matrix was approximately five times less than the erosion rate of PCPM in phosphate buffer at 7.4 pH held at 37° C. However. the rate of erosion was accelerated with increases in pH. Each matrix under test maintained its physical integrity at each pH except at pH greater than 9 where some particles were found to separate from the matrix proper. At pH 1.0, however, the erosion rate was found to be almost negligible. Accordingly, the rate of erosion is thus demonstratably affected by the pH of the environment at the site of its intended use.

A series of tests to preliminarily evaluate the cytotoxicity and mutagenicity of the degradation products released by the PCPP matrix and the PCPP-sebacic acid copolymers were conducted using the forward mutation assay of Ames et al, Mutat. Res. 31: 347-364 (1975) using mutated Salmonella typhimurium and their resistance to 8-azaguanine as a genetic marker. This mutagenicity assay also includes a test for toxicity so that the mutagenicity, if present, can be expressed quantitatively as the number of mutants per surviving cell. In this way, an independent measure of toxicity to the Salmonella bacteria could be obtained. Samples of the PCPP polymer and prepolymer were tested at 1.0 mg/ml levels both with and without the addition of mammalian metabolism enzymes. Using the techniques now uniform for this type of assay, each empirical assay was conducted in conventional format with conventional reagents and the results evaluated as described in the literature. The data reveal that both the PCPP-sebacic acid copolymers as prepared and purified, the PCPP polymeric matrix and the degradation products released by surface erosion of the PCPP matrix in physiological saline exhibited neither mutagenicity nor toxicity.

EXAMPLE III

A preferred copolymer for use as the hydrophobic polyanhydride matrix were combinations of poly(-terephthalic acid), (hereinafter "TA") and poly(sebacic acid), (hereinafter "SA") were used. TA and SA were individually mixed with excess acetic anhydride as described earlier to yield a pure recrystallized solid prepolymer. The resulting prepolymers comprising TA and SA respectively were combined in varying concentration ratios of 0:100, 30:70, 50:50, 80:20 and 100:20 TA to SA. Copolymers were then synthesized in each of these concentration ratios following an adaptation of the method of Yoda and Matsuda [Bull. Chem. Soc. Japan 32:1120-1129 (1959); Japanese Patent No. 10,944]. This technique of solution polymerization utilizes a dehydrative coupling reaction between an acyl chloride and a carboxyl group to obtain the polymer. This polymerization technique is preferable because the high melting point (372° C.) of the TA polymer and its instability (charring) at this temperature makes the melt-polycondensation methodology previously described unsuitable. Preferably, the appropriate quantity of TA and SA, such as 0.02 mole is dissolved in 400 ml of chloroform in the presence of 0.04 mole of triethylamine. Tetraphthaloyl chloride in the desired quantity, such as 0.02 mole, previously dissolved in benzene is added to a dropping funnel over a 30 minute period under vigorous agitation. This liquid admixture is allowed to react for 3 hours at room temperature and is held under a nitrogen sweep at all times. The resulting copolymer is then purified by extraction with anhydrous ether in a Soxhlet Extractor for between 2-3 hours and was then stored in a dessicator over calcium chloride.

Each of the respective copolymers, regardless of the specific TA:SA ratio concentration, were compression molded into thin slabs in the manner described previously in Examples I and II. The erosion rates for each copolymer was then evaluated by placing the copolymer matrix in phosphate buffered solutions at 37° C. The test conditions and duration were identical to those described in Example I and Figs. 1 and 2. The results indicated that the rate of erosion was inversely proportional to the concentration of TA; accordingly, the greater the TA:SA ratio, the less the rate of erosion for the matrix. It will be appreciated that the two monomers TA and SA thus present the two extremes of hydrophobicity; while SA hydrolytically degrades in atmospheric moisture, TA always remains highly resistant to hydrolysis regardless of specific conditions. By varying the concentration ratio or TA to SA in the copolymer, a matrix having a range of different degradation rates is thus obtained without regard to the degree of polymerization and without regard to the total molecular weight of either prepolymer or the copolymer itself. Additionally, by altering the TA:SA ratio concentration, the elastic properties of the matrix regardless of configuration or geometric dimensions can be altered to suit the users' needs or desires from a rigid matrix to a rubbery flexible matrix.

Each of the respective copolymers (having various concentration ratios of TA:SA) were also tested for mutagenicity and cytotoxicity using the forward mutation assay involving *Salmonella typhimurium* using 8-azaguanine resistance as a genetic marker [Skopec et al, Proc. Natl. Aca. Sci. USA 75:410-414 (1978)]. This mutagenicity assay also includes a test for toxicity so that the mutagenicity, if present, can be expressed quantitatively as the number of mutants per surviving cell. In this way, an independent measure of toxicity for the bacterial species can be obtained. Samples of each copolymer were tested at 1 mg/ml levels both with and without the addition of mammaalian metabolism enzymes. The results of this assay demonstrated that the degradation products of each copolymer, regardless of TA:SA ratio concentrations were non-mutagenic, with or without the addition of a mammalian metabolizing system. Similarly, there was no toxicity in any sample without the addition of metabolic enzymes, and there was a slight, but not significant toxicity in samples with the metabolizing system.

The present invention is not to be restricted in form nor limited in scope except by the claims appended hereto.

We claim:

1. A zero-order release rate polymeric device comprising a hydrophobic polyanhydride polymeric composition degrading by surface erosion, said composition having the formula wherein R and R' are selected from the group consisting of compositions having a molecular weight not substantially greater than 500 daltons and wherein m and n are at least 1, and at least one biologically active substance; wherein the polyanhydride is polymerized from prepolymers formed from dicarboxylic acids purified by recrystallization until the contaminants and degradation products present in the prepolymer are removed, said polymer being characterized by biocompatibility that results in minimal tissue irritation when implanted in vasculated tissue, and approximately zero order erosion and release rates of substance in vivo as a function of hydrolysis of the anhydride linkages in the polyanhydride.

2. A zero-order release rate polymeric device comprising a hydrophobic polyanhydride polymeric composition degrading by surface erosion, said composition having the formula wherein R and R' are selected from the group consisting of compositions having a molecular weight not substantially greater than 500 daltons and wherein m and n are at least 10, and at least one biologically active substance; wherein the polyanhydride is polymerized from prepolymers formed from dicarboxylic acids purified by recrystallization until the contaminants and degradation products present in the prepolymer are removed, said polymer being characterized by biocompatibility that results in minimal tissue irritation when implanted in vasculated tissue, and approximately zero order erosion and release rates of substance in vivo as a function of hydrolysis of the anhydride linkages in the polyanhydride.

3. The polymeric matrix as recited in claim 1 wherein R is identical to R'.

4. The polymeric matrix as recited in claim 1, 2 or 3 wherein R is an alkyl group comprising from 1-20 carbon atoms.

5. The polymeric matrix as recited in claim 1, 2 or 3 wherein R is an aromatic organic moiety.

6. The polymeric matrix as recited in claim 1, 2 or 3 wherein R is selected from the group consisting of p-carboxyphenoxy methane, its homologues and derivatives.

7. The polymeric matrix as recited in claim 1, 2 or 3 wherein R is selected from the group consisting of benzene and substituted benzenes.

8. The polymeric matrix as recited in claim 1, 2 or 3 wherein R is selected from the group consisting of pyridine and its derivatives.

9. The polymeric matrix as recited in claim 1, 2 or 3 wherein R is a heterocyclic aromatic composition.

10. The composition as recited in claim 1, 2 or 3 wherein R comprises terephthalic anhydride.

11. The polymeric matrix as recited in claim 1, 2 or 3 wherein R comprises sebacic anhydride.

12. The polymeric matrix as recited in claim 1 or 2 wherein R is polyterephthalic anhydride and R' comprises polysebacic anhydride.

13. The polymeric matrix as recited in claim 1, 2 or 3 wherein said biologically active substance is a pharmaceutically active drug.

14. The polymeric matrix as recited in claim 1, 2 or 3 wherein said biologically active substance is proteinaceous in composition.

15. The polymeric matrix as recited in claim 1, 2 or 3 wherein the biologically active substance has enzymatic activity.

16. The polymeric matrix as recited in claim 1, 2 or 3 wherein said biologically active substance is selected from the group consisting of antigens and antibodies.

17. The polymeric matrix as recited in claim 1, 2 or 3 wherein the biologically active substance is selected from the group consisting of polysaccharides, growth factors, hormones, anti-angiogenesis factors and interferons.

* * * * *

UNITED STATES PATENT AND TRADEMARK OFFICE
CERTIFICATE OF CORRECTION

PATENT NO. : 4,891,225

DATED : January 2, 1990

INVENTOR(S) : Langer, et al.

It is certified that error appears in the above-identified patent and that said Letters Patent is hereby corrected as shown below:

On the title page, item [75]:
In the list of inventors, insert --Robert J. Linhardt, Iowa City, Iowa; Kam Leong, Cambridge, Mass.--
Column 1, line 64, change "zeroorder" to --zero-order--.
Column 3, line 42, change "r" to --R--.
Column 5, line 14, change "ntities" to --entities--.
Column 5, line 53, change "beam" to --bean--.
Column 9, line 47, change "150300" to --150-300--.
Column 10, line 15, change "meltpressured" to --melt-pressured--.
Column 10, line 32, change "absorbence" to --absorbance--.
Column 10, line 33, change "2434" to --243--.
Column 10, line 41, change "3" to --2--.
Column 10, line 50, change "c." to --C.--.
Column 11, line 29, change "347°" to --37°--.

Signed and Sealed this

Twenty-third Day of July, 1991

Attest:

HARRY F. MANBECK, JR.

*Attesting Officer*   *Commissioner of Patents and Trademarks*